United States Patent
Murphy et al.

(10) Patent No.: US 11,482,316 B2
(45) Date of Patent: *Oct. 25, 2022

(54) SURGICAL PLANNING SYSTEM AND METHOD

(71) Applicants: Surgical Planning Associates Inc., Medford, MA (US); Stephen B. Murphy, Winchester, MA (US)

(72) Inventors: Stephen B. Murphy, Winchester, MA (US); Jens Horst Kowal, Seftigen (CH)

(*) Notice: Subject to any disclaimer, the term of this patent is extended or adjusted under 35 U.S.C. 154(b) by 109 days.

This patent is subject to a terminal disclaimer.

(21) Appl. No.: 16/740,940

(22) Filed: Jan. 13, 2020

(65) Prior Publication Data

US 2020/0152311 A1 May 14, 2020

Related U.S. Application Data

(63) Continuation of application No. 13/225,246, filed on Sep. 2, 2011, now Pat. No. 10,540,479.

(Continued)

(51) Int. Cl.
*G16H 20/40* (2018.01)
*A61B 17/58* (2006.01)
(Continued)

(52) U.S. Cl.
CPC ............... *G16H 20/40* (2018.01); *A61B 6/00* (2013.01); *A61B 17/58* (2013.01); *A61B 17/60* (2013.01); *G06Q 10/00* (2013.01); *G16H 30/20* (2018.01)

(58) Field of Classification Search
CPC ...................................................... G06Q 10/00
(Continued)

(56) References Cited

U.S. PATENT DOCUMENTS 6,200,255 B1  3/2001  Yu
6,208,974 B1*  3/2001  Campbell .............. G16H 40/63
                                                           705/3

(Continued)

FOREIGN PATENT DOCUMENTS

EP    1 406 203 A2    4/2004
WO    WO-2008/117057 A1    10/2008
(Continued)

OTHER PUBLICATIONS ip.com search, Jun. 8, 2022 (Year: 2022).*

(Continued)

*Primary Examiner* — Dilek B Cobanoglu
(74) *Attorney, Agent, or Firm* — Cesari and McKenna, LLP

(57) ABSTRACT

A system and method to receive a request for a patient-specific surgical plan, create the requested plan, and provide it to a surgeon is disclosed. A Planning server may receive information regarding a patient, such as one or more files or objects, and an order from a surgeon for a surgical plan. A Plan Development client may include a surgical planning module that accesses the one or more files or objects, and creates a computer-generated, three-dimensional model of the patient anatomy. The planning module of the Plan Development client also may create an electronic surgical plan, and may transmit the plan to the Planning server. The ordering surgeon may be notified of the availability of the plan, and may access the plan stored at the Planning server through a surgeon client. The ordering surgeon may utilize the remotely generated surgical plan during the surgical procedure on the patient.

20 Claims, 11 Drawing Sheets

Related U.S. Application Data

(60) Provisional application No. 61/508,559, filed on Jul. 15, 2011.

(51) Int. Cl.
*A61B 6/00* (2006.01)
*A61B 17/60* (2006.01)
*G06Q 10/00* (2012.01)
*G16H 30/20* (2018.01)

(58) Field of Classification Search
USPC .......................................... 705/2, 3; 600/427
See application file for complete search history.

(56) References Cited

U.S. PATENT DOCUMENTS

| | | | |
|---|---|---|---|
| 6,675,040 B1 * | 1/2004 | Cosman | G06T 3/00 600/427 |
| 8,265,949 B2 * | 9/2012 | Haddad | A61B 17/157 705/2 |
| 8,267,938 B2 | 9/2012 | Murphy | |
| 8,382,765 B2 * | 2/2013 | Axelson | A61B 34/10 606/88 |
| 8,444,651 B2 * | 5/2013 | Kunz | A61B 17/1757 606/87 |
| 8,473,305 B2 * | 6/2013 | Belcher | G16H 40/63 705/2 |
| 8,986,309 B1 | 3/2015 | Murphy | |
| 2005/0278195 A1 * | 12/2005 | Getz | G06Q 10/10 705/2 |
| 2007/0219561 A1 | 9/2007 | Lavallee | |
| 2008/0235052 A1 * | 9/2008 | Node-Langlois | G16H 20/40 705/3 |
| 2008/0319448 A1 | 12/2008 | Lavallee | |
| 2009/0209884 A1 | 8/2009 | Van Vorhis | |
| 2010/0274579 A1 * | 10/2010 | Marten | G16H 10/60 705/2 |
| 2010/0303313 A1 * | 12/2010 | Lang | A61F 2/30756 382/128 |
| 2011/0137680 A1 * | 6/2011 | Sweeney | G06Q 10/06 705/3 |

FOREIGN PATENT DOCUMENTS

| | | |
|---|---|---|
| WO | WO-2009/087214 A1 | 7/2009 |
| WO | WO-2009/106812 A1 | 9/2009 |
| WO | WO-2011/051649 A1 | 5/2011 |

OTHER PUBLICATIONS

Building Anatomical Models from CT and MRI Scans for Orthopedic Preoperative Planning and Custom Implant Construction, Sam M. Wood, III, et al., Proceedings of the 1997 16 Southern Biomedical Engineering Conference (pp. 466-469), IEEE Conference (Year: 1996).*

"Notification of Transmittal of the International Search Report and the Written Opinion of the International Searching Authority, or the Declaration," International Filing Date: Jul. 5, 2012, International Application No. PCT/US2012/045488, Applicant: Murphy, Stephen B., dated Sep. 5, 2012, pp. 1-10.

* cited by examiner

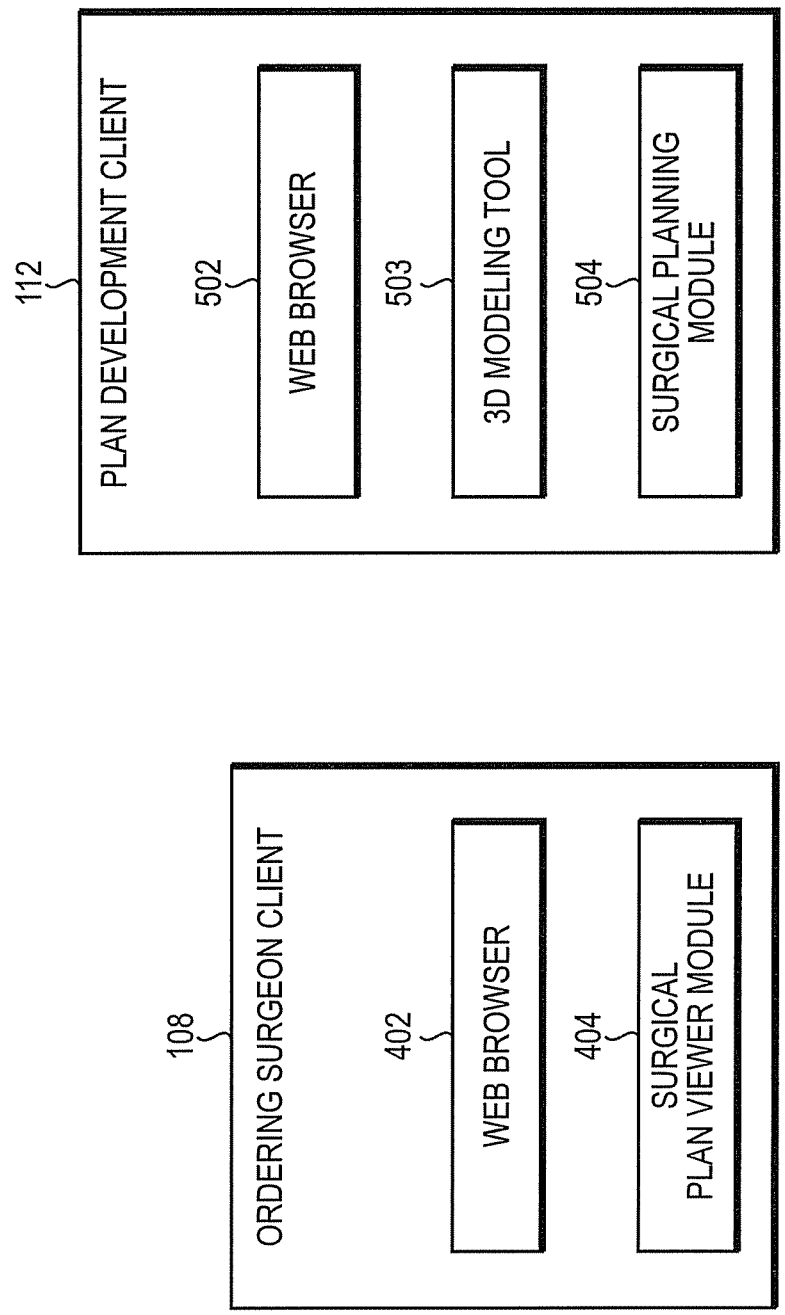

MENU
- Home ~704
- Purpose
- Contact
- Ordering
- Instructions For Use
- FAQ
- Download Documents
- Download Viewer Software
- Upload Data ~706
- Download Planning ~708
- Invoices

LOGIN

[LOGOUT]

Submit a Planning Request

Patient Last Name ⓣ  * ~712
Patient First Name ⓣ * ~714
Patient Date of Birth ⓣ * ~716
Location  * [Select ▾] ~718 ~720
Date First Surgery ⓣ * ~722
Date Second Surgery ⓣ ~724
Assigned Surgeon ⓣ *
Data to Upload ⓣ [Browse...] ~728
~726
[Submit] ~730

Press "Submit" to see all plannings assigned to you. You can use the "Patient Last Name" or the "Planned Side" field to narrow down your search result.

| Download Plannings | | | | |
|---|---|---|---|---|
| Patient Last Name ⓘ | | | | |
| Planned Side ⓘ | - Select - ▽ 1004 | | | |
| Submit 1006 | | | | |
| Patient Last Name | Patient First Name | Planned Side | Left Side Plan | Right Side Plan | View |
| Stevens | Ray | Right | | StevensRtPlan.zip | View |
| Jones | Bob | Left | JonesLftPlan.zip | | View |
| | | | | 1010b | 1010a |
| ⇤ ◁ Page [1] of 1 ▷ ⇥ ↻ | | | | Displaying 1-19 of 19 |

(Patient Last Name field labeled 1002; 1000 overall; 1008 points to table)

FIG.10

SURGICAL PLANNING SYSTEM AND METHOD

CROSS-REFERENCE TO RELATED APPLICATIONS

The present application is a continuation of commonly assigned copending U.S. patent application Ser. No. 13/225,246, filed on Sep. 2, 2011, by Stephen B. Murphy and Jens Horst Kowal for SURGICAL PLANNING SYSTEM AND METHOD, which claims priority from U.S. Provisional Patent Application Ser. No. 61/508,559, filed Jul. 15, 2011, by Stephen B. Murphy for SURGICAL PLANNING SYSTEM AND METHOD, the contents of both of which are incorporated by reference herein in their entirety.

SUMMARY OF THE INVENTION

Briefly, the present invention relates to a system and method for receiving a request for one or more patient-specific surgical plans, creating the requested plans, and providing the plans to an ordering surgeon. As part of the request for a surgical plan, a Planning server may receive information regarding a patient, such as one or more digital images of the portion of the patient's anatomy that is to be operated on. The Planning server may also receive an order from a surgeon, an imaging technologist, or a sales representative, among others, for a surgical plan. A Plan Development client may include a surgical planning module that accesses the one or more digital images from the Planning server, and creates a computer-generated, three-dimensional model of the patient anatomy. The planning module of the Plan Development client also may create an electronic surgical plan, and may transmit the plan to the Planning server. The ordering surgeon may be notified of the availability of the plan, and may access the plan stored at the Planning server through client device associated with the surgeon. The ordering surgeon may review, modify according to specific needs, and utilize the remotely generated surgical plan during the surgical procedure on the patient.

BRIEF DESCRIPTION OF THE DRAWINGS

The invention description below refers to the accompanying drawings, of which:

FIG. 4 is a functional block diagram of an ordering surgeon client in accordance with an embodiment of the present invention;

FIG. 5 is a functional block diagram of a plan development client in accordance with an embodiment of the present invention;

FIG. 7 is a schematic illustration of a request web page in accordance with an embodiment of the present invention;

FIG. 10 is a schematic illustration of a surgical plan download web page in accordance with an embodiment of the present invention.

DETAILED DESCRIPTION OF AN ILLUSTRATIVE EMBODIMENT

Figure 1:
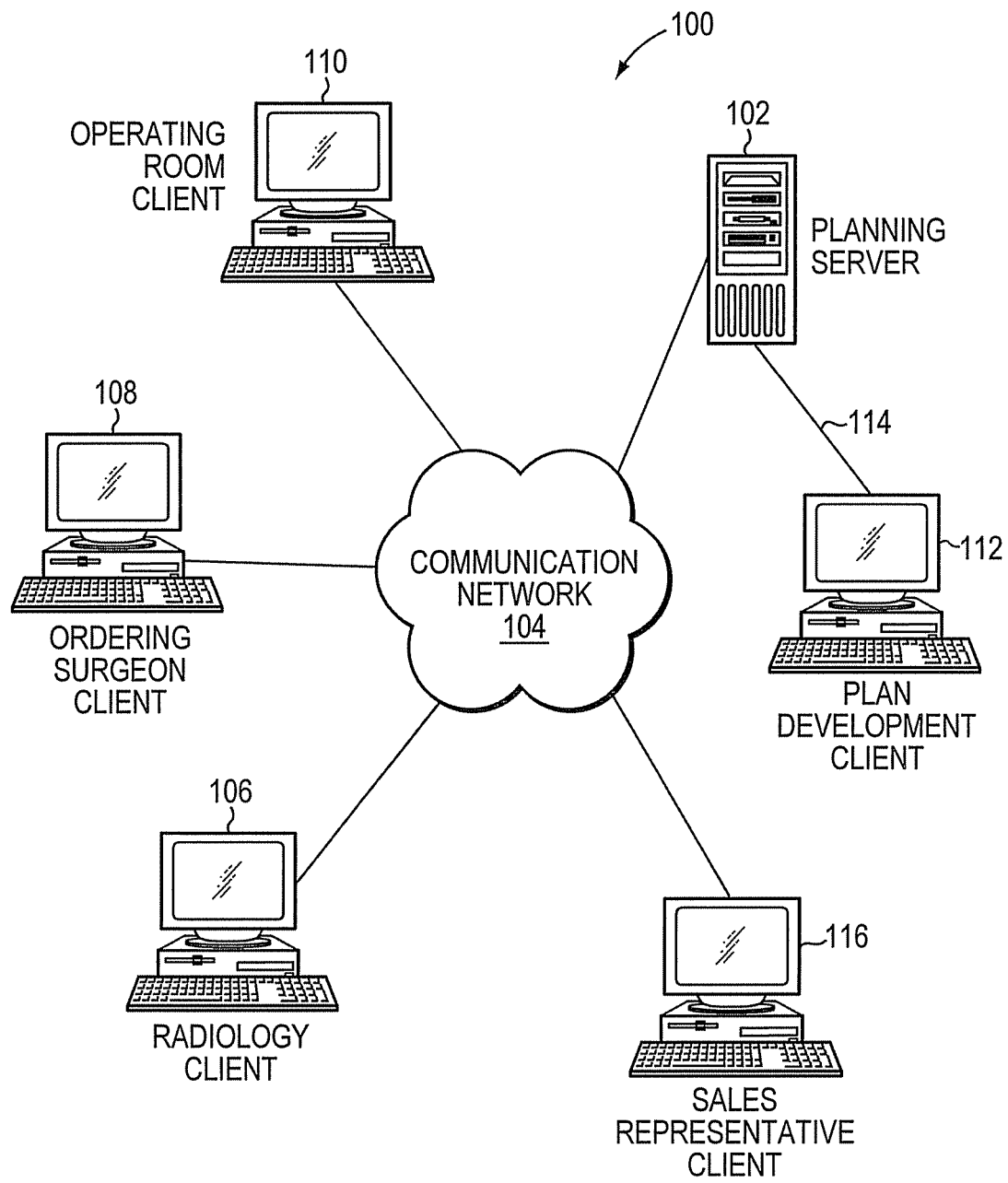
FIG. 1 is a highly schematic illustration of an environment in accordance with an embodiment of the present invention.

FIG. 1 is a schematic illustration of an environment 100 in which the present invention may be utilized. The environment 100 may include a Planning server 102 that may be coupled to a communication network 104. Also coupled to the communication network 104 may be a plurality of data processing devices that are associated with hospitals, operating rooms, and/or surgeons. Specifically, a Radiology client 106 may be located in a Radiology department of a hospital at which a surgical procedure, such as total hip replacement (THR) surgery, will be performed on a patient. An Ordering Surgeon client 108 may be located in the office of the surgeon that will be performing the procedure. An Operating Room (OR) client 110 may be located in an operating room of the hospital at which the surgical procedure will be performed. Clients 106, 108, and 110 may each be coupled to the communication network 104, e.g., through one or more wired and/or wireless networks or other data transmission connections. A Plan Development client 112 may be directly coupled to the Planning Server 102 by a data link 114. Alternatively, the Plan Development client 112 may communicate with the Planning Server 102 through one or more networks, including the communication network 104. The environment 100 may also include a Sales Representative or Operative Room Administrative client 116 coupled to the communication network 104.

It should be understood that the Radiology client 106 may be located in a different location than the hospital at which the surgery is to be performed. For example, the Radiology client 106 may be located at an imaging service facility or other laboratory or diagnostic facility that is independent of the hospital.

It should be understood that the communication network 104 may include one or more interconnected data networks such as a Local Area Network (LAN), a Wide Area Network (WAN), a Metropolitan Area Network (MAN), the Internet, a Virtual Private Network (VPN), a wireless network, a cellular telephone network, the public switched telephone network (PSTN), etc.

As described herein, the Planning server 102 provides services to one or more clients, i.e., electronic clients, including clients 106-112. The Planning server 102 may be geographically located remotely from the clients 106, 108, 110, 112 and 116. It should be understood that other, possibly far more complex, network designs and/or client-server architectures may be implemented. For example, the environment 100 may include other clients, such as an invoicing or billing client.

Figure 2:
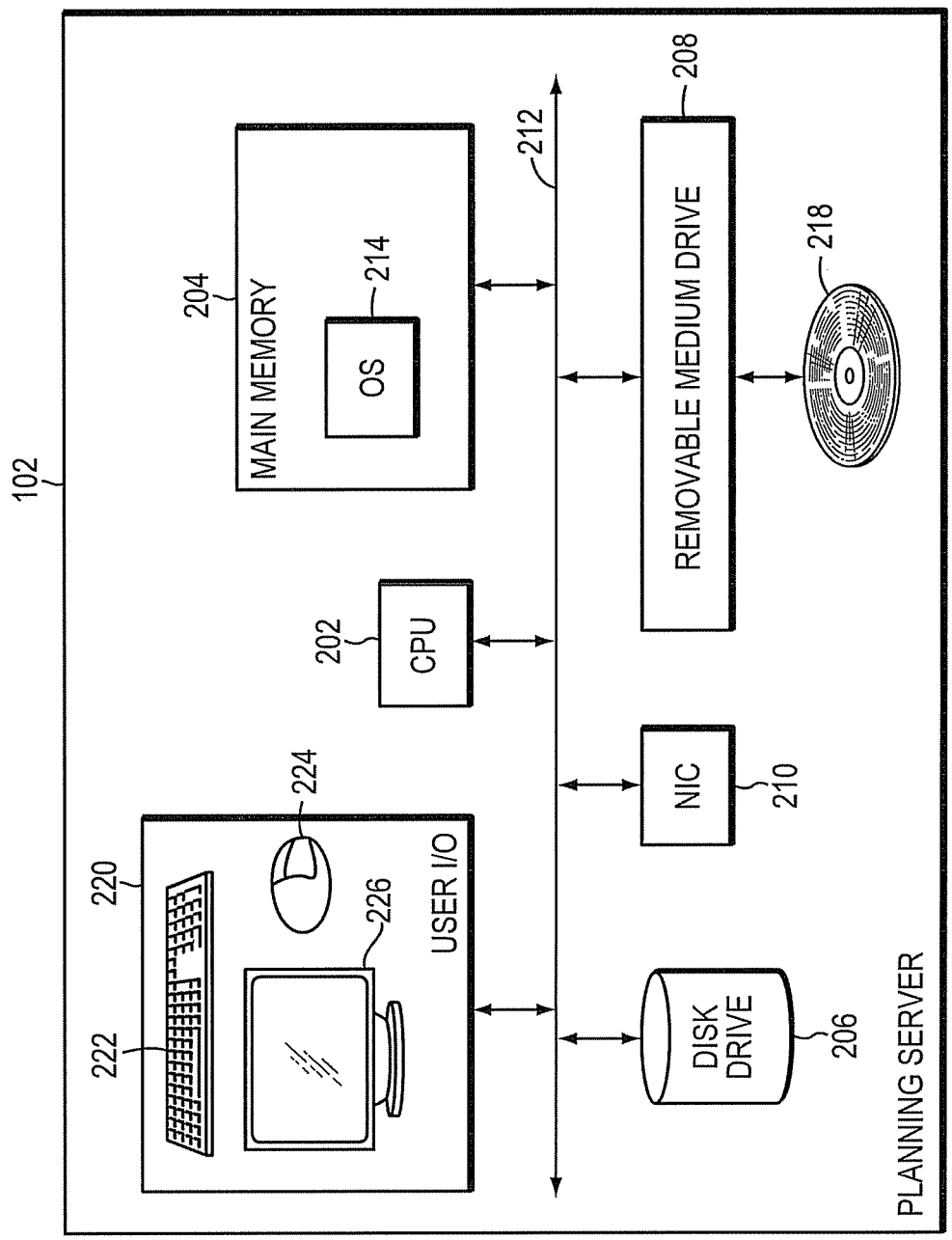
FIG. 2 is a schematic illustration of a server in accordance with an embodiment of the present invention.

FIG. 2 is a schematic hardware illustration of the Planning server 102. The Planning server 102 may include one or more processors or other processing logic, such as a central processing unit (CPU) 202, a main memory 204, one or more storage devices, such as a disk drive 206, a removable medium drive 208, and one or more network interface cards (NICs) 210 that are interconnected by one or more busses, such as a system bus 212. The main memory 204 may store a plurality of programs, libraries or modules, such as an operating system 214, and one or more applications running on top of the operating system 214. The removable medium drive 208 is configured to accept and read a computer readable medium 218, such as a CD, DVD, floppy disk, solid state drive, tape, flash memory or other medium. The removable medium drive 208 may further be configured to write to the computer readable medium 218.

The Planning server 102 also may include and/or be accessible by a device having a user input/output (I/O) 220. The user I/O 220 may include a keyboard 222, a pointing device, such as a mouse 224 and a display 226. It should be understood that other or additional user I/O may be provided, such as a touch screen, a touch pad, etc.

Suitable servers include the ProLiant and Integrity series of servers from Hewlett Packard Co. of Palo Alto, Calif., and the PowerEdge series of servers from Dell Inc. of Round Rock, Tex., among others.

Suitable processors may include single processor architectures, dual or quad core processor architectures, microprocessors, digital signal processors (DSPs), programmable logic devices, etc., or various combinations thereof.

Suitable operating systems 214 include the Windows series of operating systems from Microsoft Corp. of Redmond, Wash., the Linux operating system, the MAC OS® series of operating systems from Apple Inc. of Cupertino, Calif., and the UNIX® series of operating system, among others.

It should be understood that the Planning server 102 of FIG. 2 is meant for illustrative purposes only, and that the present invention may be used with other computer systems, processing systems or computational devices.

It should further be understood that the clients 106, 108, 110, and 112 of FIG. 1 may include similar hardware components as illustrated in FIG. 2 for the Planning server 102. Suitable client devices include personal computers (PCs), workstations, laptops, palm computers and other portable computing devices, smart phones, tablet computers, electronic readers (e-readers) etc.

Figure 3:
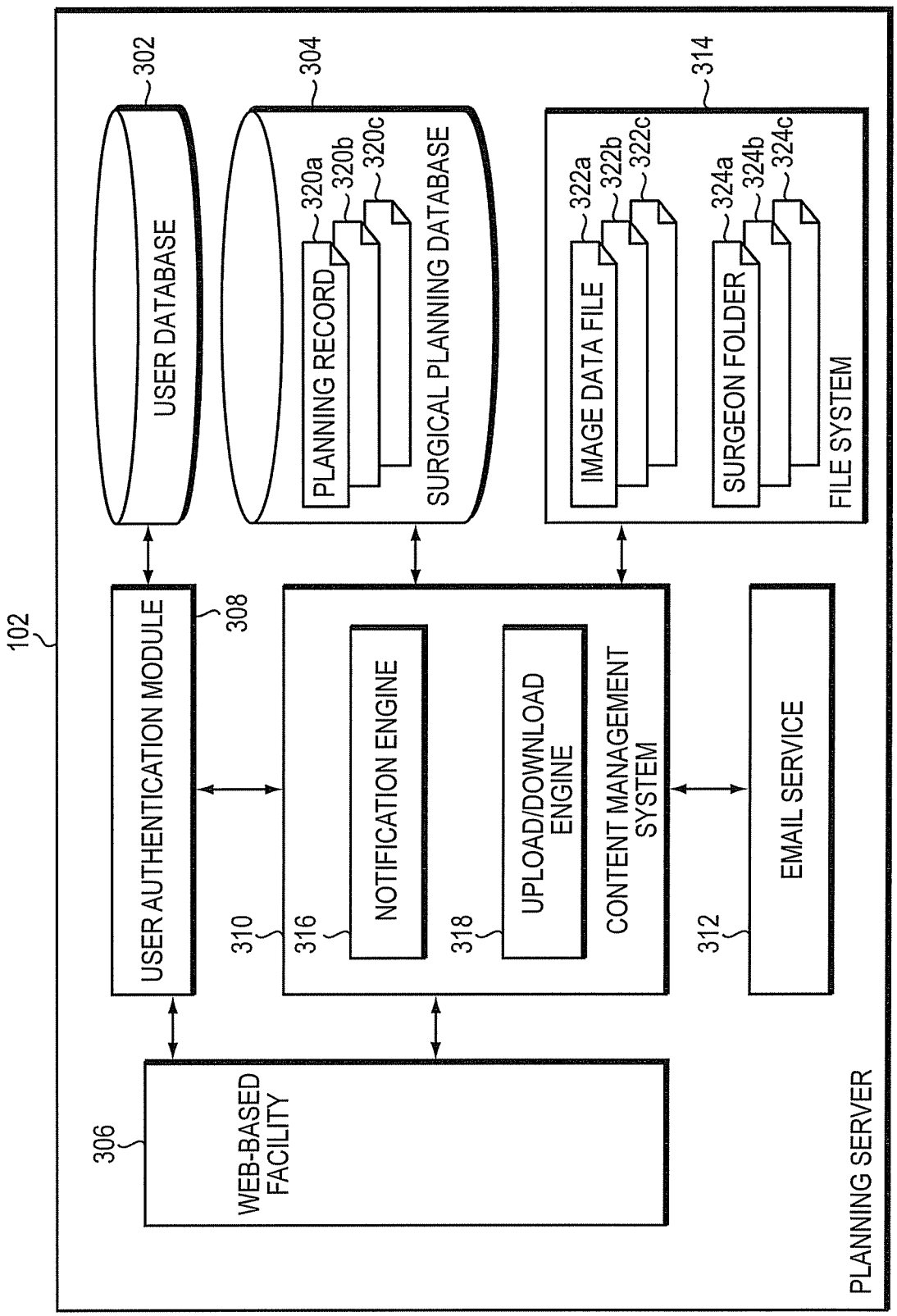
FIG. 3 is a functional block diagram of a server in accordance with an embodiment of the present invention.

FIG. 3 is a schematic, functional illustration of the Planning server 102. The Planning server 102 may include one or more databases, such as a User database 302, and a Surgical Planning database 304. The Planning server 102 may also include one or more modules, such as a web-based facility 306, a user authentication module 308, a content management system 310, an email service 312, and a file system 314. The content management system 310 may include one or more modules, such as a notification engine 316, and an upload/download engine 318. The User database 302 may store a plurality of user authentication records, which may include user names and passwords. The User database 302 may also include contact information such as email address, telephone number, etc., among other information. The Surgical Planning database 304 may include a plurality of planning records, such as planning records 320a-c. The file system 314 may include a plurality of directories, folders, and files, such as a plurality of image data files 322a-c, and a plurality of surgeon directories or folders 324a-c.

Clients, such as Radiology client 106 (FIG. 1), Surgeon client 108, OR client 110, and Plan Development client 112 may access the Planning server 102 via the web-based facility 306. The web-based facility 306 may provide functionality and services of a web server program, such as accepting Hyper Text Transport Protocol (HTTP) requests from clients, and providing HTTP responses to those clients.

It should be understood that the functional diagram of FIG. 3 is meant for illustrative purposes and that other server configurations may be used with the present invention. For example, the content management system 310 may include other components, such as a database management system (DBMS), the user authentication module may be incorporated into the content management system, the user and surgical planning databases may be combined into a single database, the image data files, may be stored in one or more of the databases, etc.

In an embodiment, the Planning server 102 may be implemented as a virtual private server. Alternatively, the Planning server 102 may be implemented as one or more dedicated physical servers, such as two or more servers geographically separated from each other to provide redundancy and backup to the operations of the Planning server 102.

It should further be understood that the functionality of the Planning server 102 may be implemented in other ways. For example, the functionality may be distributed and/or duplicated across a plurality of servers, such as in a server farm or cloud computing arrangement, among others.

Suitable web server programs for use with the present invention include Apache from the Apache Software Foundation, and Internet Information Services (IIS) from Microsoft Corp., among others.

Suitable database management systems for use with the present invention include the Oracle Database series of relational database management systems (RDBMSs) from Oracle Corp. of Redwood Shores, Calif., and the Microsoft SQL® series of RDBMS from Microsoft Corp., and MySQL, among others.

Suitable email services include the Outlook mail client from Microsoft Corp., the Thunderbird mail client from the Mozilla Foundation, etc. It should be understood that instead of or in addition to the email service 312, the planning server 102 may include other communication services, such as an instant messaging service, a text messaging service, an automated voice calling service, etc.

In an embodiment, information may be securely stored in the databases 302, 304, and in the file system 314. For example, users, such as ordering surgeons may need to be authenticated to the Planning server 102 before being granted access to the server, and access by an ordering surgeon may be limited to those records, image data and surgical plans associated with that ordering surgeon. In an embodiment, each ordering surgeon may select or be given one or more username and password combinations.

Suitable content management systems include the Joomla! Content Management System from the Joomla Project, and the Drupal Content Management System from the Open Source Community, among others. Furthermore, the Planning server 102 may be a virtual private server, a dedicated web host server, or a dedicated server, among other options.

FIG. 4 is a schematic, functional illustration of the Ordering Surgeon client 108. The client 108 may include one or more applications or modules. In particular, the client 108 may include a web browser 402, and a surgical plan viewer module 404.

FIG. 5 is a schematic, functional illustration of the Plan Development client 112. The client 112 may include one or more applications or modules. In particular, the client 112 may include a web browser 502, a three-dimensional (3D) modeling tool 503, and a surgical planning module 504.

Suitable web browsers include Internet Explorer from Microsoft, Chrome from Google Inc. of Mountain View, Calif., and Firefox from the Mozilla Foundation, among others.

The web-based facility 306, user authentication module 308, content management system 310, email service 312, and file system 314 of the planning server 102, as well as the web browser 402 and surgical plan viewer module 404 of the ordering surgeon client 108, and the web browser 502, 3D modeling tool 503, and surgical planning module 504 of the plan development client 112 may each comprise registers and combinational logic configured and arranged to produce sequential logic circuits. In an embodiment, the web-based facility 306, user authentication module 308, content management system 310, email service 312, and file system 314 of the planning server 102, as well as the web browser 402 and surgical plan viewer module 404 of the ordering surgeon client 108, and the web browser 502, 3D modeling tool 503, and surgical planning module 504 of the plan development client 112 are or include software modules or libraries containing program instructions pertaining to the methods described herein, that may be stored on computer readable media, such as computer readable medium 218, and executable by one or more processing elements, such as CPU 202. Other computer readable media may also be used to store and execute these program instructions. In alternative embodiments, various combinations of software and hardware, including firmware, may be utilized to implement the present invention.

Figure 6A:
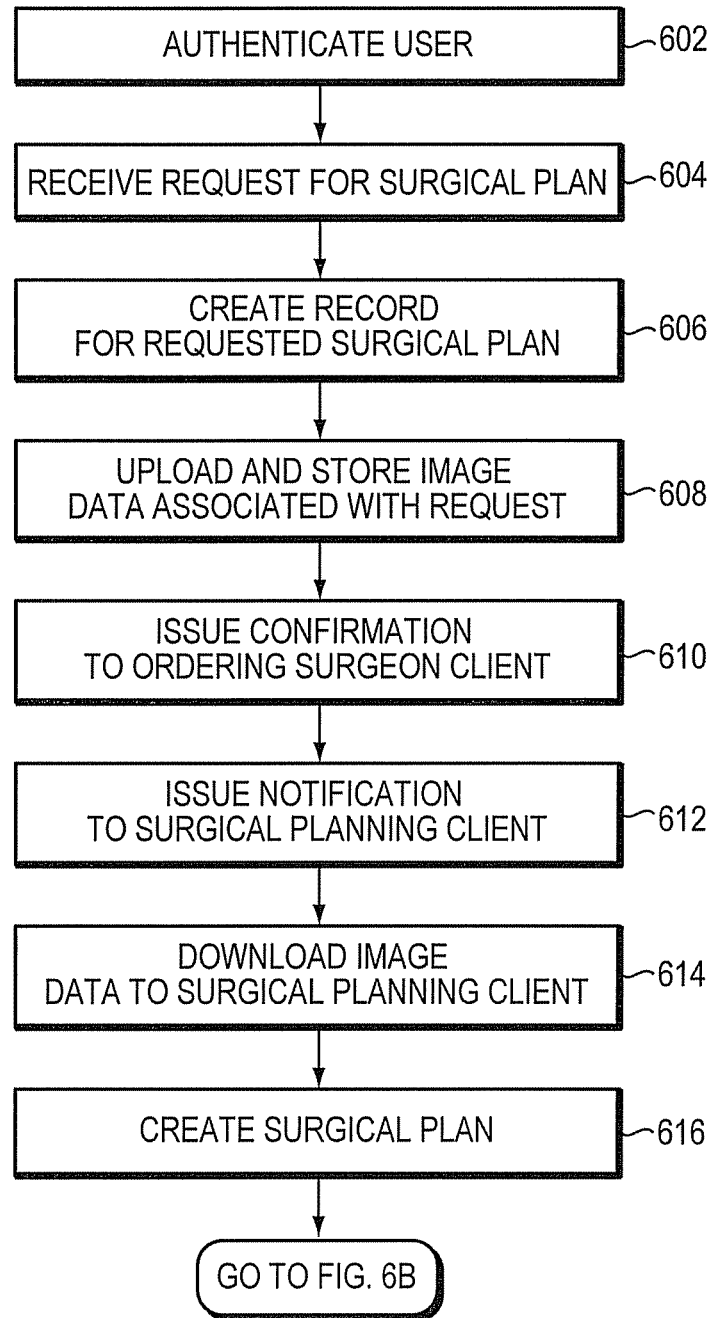
FIGS. 6A and 6B are a flow diagram of a method in accordance with an embodiment of the present invention.
Figure 6B:
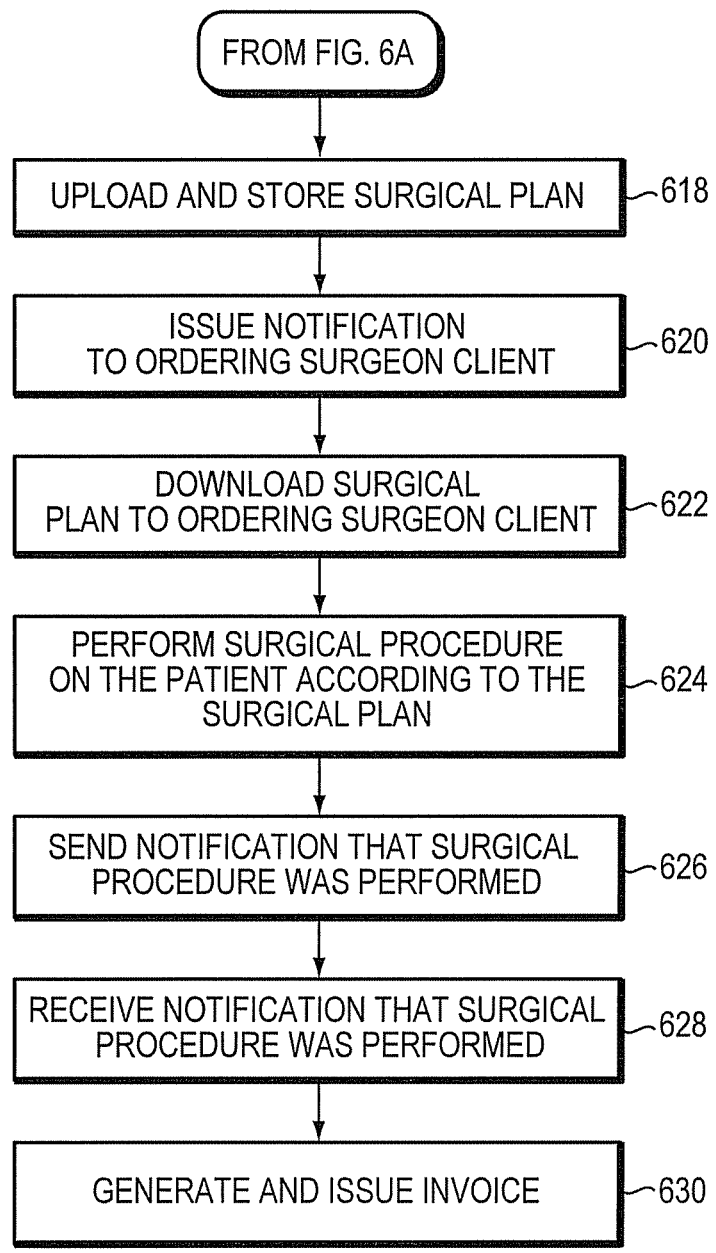

FIGS. 6A and 6B are a flow diagram of a method in accordance with an embodiment of the invention. A patient may be diagnosed with a medical condition that requires surgery. In preparation for the surgical procedure, one or more data gathering procedures may be performed. For example, a blood or other sample may be taken from the patient and analyzed. Additionally or alternatively, a cardiac stress test, an electrocardiogram, an echocardiogram, or other heart test may be performed on the patient and the results obtained. Furthermore, one or more digital images, such as Computed Tomography (CT), Magnetic Resonance Imaging (MRI), conventional radiographs (X-rays), or ultrasonic images, may be taken of the patient; specifically, that portion of the patient's anatomy on which the surgery is to be performed. It should be understood that any diagnostic test or measurement, particularly one that improves dimensional understanding about the specific portion of the patient's anatomy to be operated upon, may be performed and used for patient-specific planning.

For example, a patient may be diagnosed with hip joint failure, and may require total hip replacement (THR) surgery either on the left hip, the right hip, or both hips. In this case, one or more low cost, low dose CT scans of the patient's hip may be taken by a Radiology department, which may or may not be located at the hospital at which the THR surgery will be performed. The one or more digital images (radiographic, ultrasonic, magnetic, etc.) may be taken on the day of the patient's preoperative visit or at any time prior to surgery. The one or more digital images may provide three-dimensional information regarding the surface and/or structure of the patient's hip.

A technician or other person from the hospital's radiology department may utilize the Radiology client 106 to access the Planning server 102, and upload the one or more digital images to the Planning server 102. Specifically, the technician may use a web browser on the Radiology client 106 to navigate to a web domain hosted by the Planning server 102. The web-based facility 306 of the Planning server 102 may present a home page that includes a menu of available options for display by browser application at the Radiology client 106. The technician may select an "Upload Data" option from the menu. In response, the web-based facility 306 may request that the technician log in to the Planning server 102 by presenting a login page having data fields for receiving a username and a password. In an embodiment, the technician will have previously established an account that includes a username and password. Accordingly, the technician may enter this information (username and password) in the respective fields of the login page. In response, the user authentication module 308 of the Planning server 102 may authenticate the technician, as indicated at block 602.

If the technician is authenticated to the Planning server 102, the web-based facility 306 may establish a secure connection with the Radiology client 106, and may present a request web page for display at the Radiology client 106. FIG. 7 is a schematic illustration of a request web page 700 that may be generated by the web-based facility 306 and presented on the Radiology client 106. The request web page 700 may include a navigation menu 702 having a plurality of selectable options for navigating around the website provided by the web-based facility 306, such as a Home button 704, an Upload Data button 706, and a Download Planning button 708, among others. As indicated above, the request web page 700 may be presented in response to the technician selecting the Upload Data option button 706 in the menu 702. The request web page 700 may include a request dialog 710 having plurality of fields for receiving information from the technician. In an embodiment, the request dialog 710 of the request web page 700 may include:
  a Patient Last name field 712;
  a Patient First name field 714;
  a Patient date of birth field 716;
  a Location of the Surgery field 718 (which may have a drop down menu of available locations such as left side, right side or both in the case of THR surgery);
  a Date of First Surgery field 720;
  a Date of Second Surgery field 722;
  an Assigned Surgeon field 724; and
  a Data to Upload field 726.

It should be understood that additional or other information, such as the sex of the patient, the age of the patient, etc., may be requested.

The technician enters the requested information in the fields 712-726. In the Assigned Surgeon field 724, the technician may type in the surgeon's name. The Data to upload field 726 may include a "Browse" or other command button 728, which if selected by the technician, presents a dialog box (not shown) that allows the technician to navigate through the directories and folders located on the Radiology client 106 (or on other computers, servers or other data processing machines accessible from it) in order to select one or more data files or objects to be uploaded to the Planning server 102.

The request page 700 may also include a Submit or other command button 730 that may be selected by the technician, after entering the requested information, and identifying the one or more data files or objects. In response to entering the submit command, the request for a surgical plan, created by the technician, is received at the planning server 102, as indicated at block 604.

The content management system 310 may cooperate with the surgical planning database 304 to create a new record 320 for the request, as indicated at block 606. In addition, the upload/download engine 318 may upload the one or more data files or objects, such as image files, identified in the request from the Radiology client 106, and store them in an image data file 322 in the file system 314, as indicated at block 608.

Figure 8:
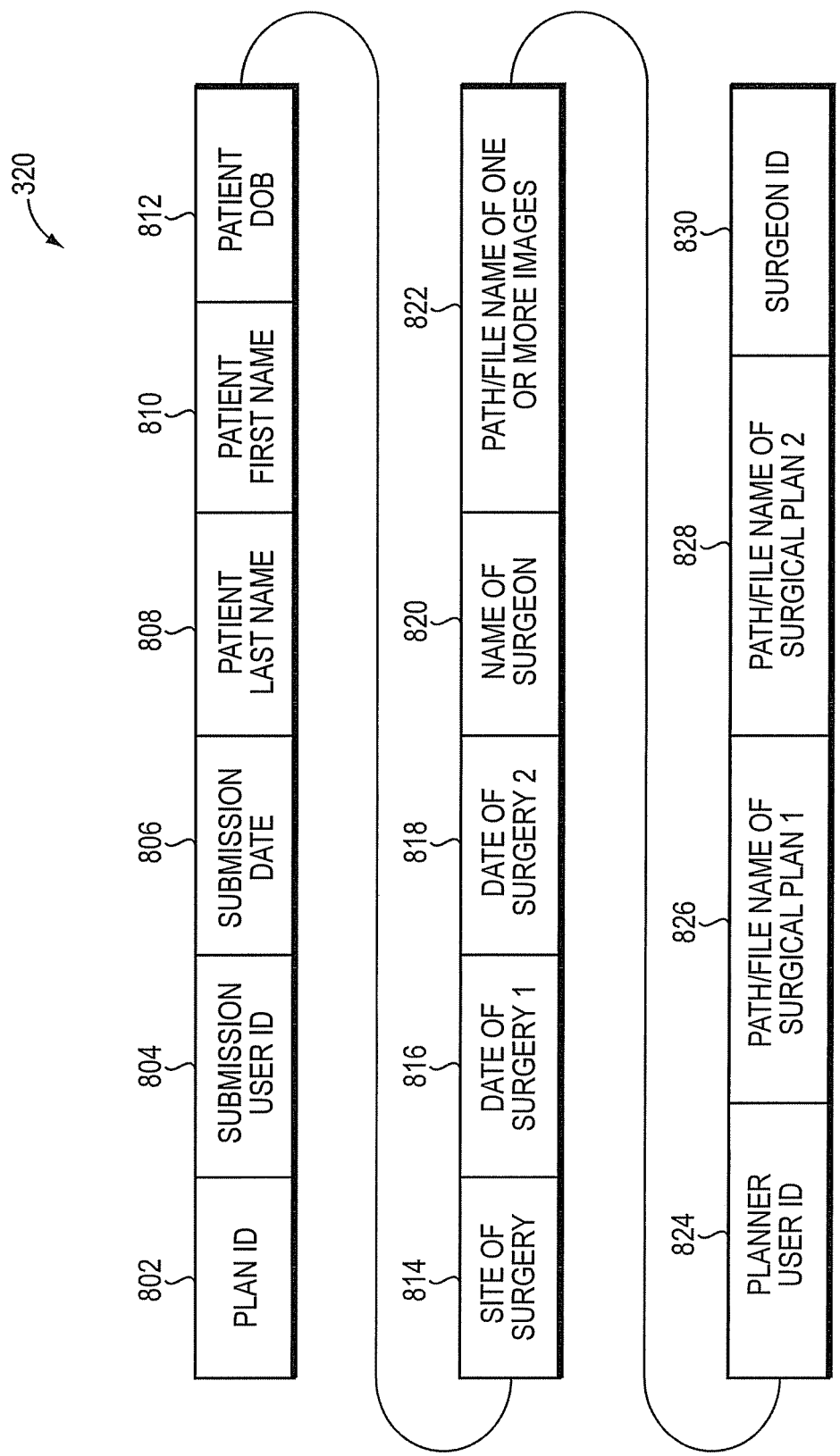
FIG. 8 is a schematic illustration of a data record in accordance with an embodiment of the present invention.

FIG. 8 is a schematic illustration of a planning record 320. The planning record 320 may include a plurality of fields or cells for storing information. Specifically, the planning record 320 may include a Plan Identifier (ID) field 802 that contains a value, such as a number, that is automatically generated by the content management system 310 to uniquely identify the record 320 in the surgical planning database 304. The planning record 320 may also include a Submission User ID field 804, which may be automatically populated by the content management system 310 with the username or other identifier of the person submitting the request, e.g., the technician. The planning record 320 may also include a Submission date field 806, which may be automatically populated by the content management system 310 with the date the request is submitted to the Planning server 102. The planning record 320 may also include a Patient Last name field 808, a Patient First name field 810, and a Patient date of birth (dob) field 812, which may be populated with information from the request by the content management system 310.

The planning record 320 may also include a Site of Surgery field 814, which may be populated with information from the request, for example, information entered into the Location field 718 (FIG. 7) of the request. For example, for THR surgery, field 814 may contain "right", "left", or "both". The planning record 320 may also include one or more fields for storing the date(s) of the surgery, such as a Date of Surgery 1 field 816, and a Date of Surgery 2 field 818, which may be populated with information contained in the request, such as information from the Date of First and Second Surgery fields 720, 722 of the request. The planning record 320 may also include the name of the surgeon who will perform the surgery in a Name of Surgeon field 820, which may be populated with information from the Assigned Surgeon field 724 of the request. The planning record 320 may also include a path/file name field 822, which contains the path and file name of the one or more data files or objects, such as images, uploaded to the Planning server 102. The recorded path and file name may identify the location of the data file or object, as uploaded and stored in the file system 314 of the Planning server 102.

The planning record 320 may also include additional fields that are populated once a surgical plan has been created in response to the request. For example, the record 320 may include a Planner User ID field 824 that contains an ID assigned to the surgical planner that creates the surgical plan for the request. The planning record 320 may also include a path/file name of surgical plan 1 field 826, and a path/file name of surgical plan 2 field 828, which may be loaded with the paths and file names of surgical plans created for surgical procedure associated with the record 320. The planning record 320 may also include a Surgeon ID field 830, which may be loaded with an ID assigned to the surgeon who will be performing the surgical procedure, and who will be able to access the first and second surgical plans through the Planning server 102.

It should be understood that the planning record 320 may include other fields, such as a status field, which may be used to indicate whether a particular record is in a pending state, i.e., awaiting a surgical plan, or in a completed state, i.e., associated with one or more surgical plans.

As indicated, the fields of the planning record 320 may be populated by the content management system 310 based on information contained in the request, and on information received from the surgical planner who creates the surgical plan.

The content management system 310 in cooperation with the email service 312 may issue a confirmation email to the technician (and/or to the surgeon identified by the technician) indicating that a request for a surgical plan has been received by the Planning server 102, as indicated at block 610. The content management system 310 and email service 312 may also issue a notification to a planning surgeon that a new request has been received, as indicated at block 612.

It should be understood that a request for a surgical plan may be made by the surgeon who will be performing the surgical procedure through the Ordering Surgeon client 108, instead of by the technician. In a further embodiment, the technician and/or ordering surgeon may append additional information to the request, such as notes prepared by the surgeon regarding particular aspects of the procedure itself, or of the patient, such as the position of the patient during the surgery, one or more desired locations or orientations of prosthetic components, such as an acetabular cup, etc.

It should also be understood that the request may be edited, for example, to change the date or location of the proposed surgery. Further, a new request may be made that refers to a previously submitted image data set. For example, if a CT study was submitted for a THR surgery on the patient's right side, and subsequently, surgery on the left side, for which the CT study is also useful, is desired, a planning request may be submitted with reference to the surgery that was previously performed so that the correct image data may be retrieved without having to upload the data a second time.

Next, a surgical planner, such as an experienced surgeon or other person, may utilize the Plan Development client 112 to access the newly created request. In particular, the surgical planner may log into the Planning server 102, and access the new request. In an embodiment, the surgical planner may enter the patient's name, and the content management system 310 may query the surgical planning database 304 for the record 320 associated with that patient. Alternatively, the surgical planner may cause other searches to be performed, such as a search based on the name of the surgeon performing the procedure, a search based on the date of the procedure, etc. In addition, rather than perform a search, the surgical planner may logon to the Planner server 102 and view all open or pending requests for surgical plans. The request, as presented on the Plan Development client 112, may include a hyperlink for the one or more image files. In response to the surgical planner selecting this hyperlink, the upload/download engine 318 may download the one or more data files or objects, such as one or more image data files 322, from the file system 314 to the Plan Development client 112, as indicated at block 614. The surgical planner may then utilize the one or more files or objects, e.g., images, to create a surgical plan for the procedure, as indicated at block 616.

In an embodiment, the surgical planner may utilize the 3D modeling tool 503 of the Plan Development client 112 to create a computer-generated, three-dimensional model of the patient's anatomy, such as the patient's hip, based on the one more digital images uploaded to the Planning server 102 from the Radiology client 106.

The Plan Development client 112 also may run surgical planning software, such as the surgical planning module 504 (FIG. 5). The surgical planner operating the Plan Development client 112 may utilize the surgical planning module 504 to create an electronic surgical plan for the surgical procedure that is to be performed on the patient. For example, the surgical planner may create a plan for inserting one or more prosthetic or surgical components, such as an acetabular cup component, into the patient's hip during THR surgery, using one or more surgical instruments.

In an embodiment, the surgical planner operating the surgical planning module 504 may establish a standard pelvic coordinate system, such as the anterior pelvic plane, for the 3-D, computer-generated model of the pelvis. A patient-specific coordinate system for use by the one or more surgical instruments may also be established, for example, by using three points on the 3-D model of the patient's pelvis.

A suitable surgical instrument and its use is described in copending, commonly owned U.S. patent application Ser. No. 12/134,545, filed Jun. 6, 2008, for a Method and Apparatus for Determining Acetabular Component Positioning by Stephen Murphy, which is hereby incorporated by reference in its entirety.

In an embodiment, the surgical planning module 504 is used by the surgical planner operating the Plan Development client 112 to calculate one or more inputs and/or adjustments to be made on the one or more surgical instruments. The inputs and/or adjustments may be based, at least in part, on the 3-D model of the pelvis that was created, on some or all of the patient-specific information, and/or on statistical information known to or accessible by the surgical planner. For example, the inputs and/or adjustments may be used in order to make a direction indicator of a surgical instrument point in a direction of acetabular cup orientation, as desired by ordering surgeon and/or as intended by the surgical planner. Furthermore, knowledge of supine and/or standing pelvic tilt, which may be provided as part of the patient-specific information, can be incorporated in the adjustments to be made to the surgical instrument.

The surgical plan may thus include a series of inputs or adjustments to be made to one or more surgical instruments before or during the procedure. The surgical plan may further include instructions for setting up and using the one or more surgical instruments during the procedure. In other embodiments, the surgical plan may be or may include machine instructions, such as executable code, for operating one or more machines, such as a surgical tool or other machine to assist during the surgical procedure. The surgical plan may even include machine instructions to be executed by a robotic surgical tool that will perform all or part of the procedure. For example, the surgeon may register a body part of the patient in accordance with one or more requirements, and once the body part is registered, an active, semi-active, or haptic robot may be used to perform all or part of the planned procedure operating according to instructions in the surgical plan or a locally updated surgical plan according to additional desires input by the surgeon. The robot, moreover, may be controlled from the Planning server, for example, through the OR client 110 or another data processing device. In addition to controlling a surgical robot, the surgical plan may provide instructions for controlling a free-hand surgical device, such as a rotating tool, to turn on when it is in a location where cutting is to be performed and either turn off or through deployment of a protective sheath when it is in a location where cutting should not take place.

Exemplary surgical robots include the surgeon-controlled robotic arms from Mako Surgical Corp. of Fort Lauderdale, Fla. Exemplary free-hand tools include the freehand sculptor from Blue Belt Technologies, Inc. of Pittsburgh, Pa.

In an embodiment, the surgical plan may include one or more 3D printer files that may be used to operate a locally controlled 3D printer to create a single-use, patient-specific instrument or prosthetic component, such as a component designed to mate with the patient's anatomy, such as the patient's hip, knee or other joint. For example, the component may fit uniquely onto patient-specific anatomy in or adjacent to a joint of the patient, and provide the specific orientation and location of a drill guide to be used during the surgical procedure on the patient. The surgeon or a technician may utilize the one or more 3D printer files to run the 3D printer and construct the patient-specific component. The 3D printer may be located at the hospital at which the surgery is to be performed or it may be located at another facility, such as a quality-controlled manufacturing facility that is local to the hospital.

A suitable component or template is described in co-pending U.S. patent application Ser. No. 12/263,808, filed Nov. 3, 2008 for an ACETABLULAR TEMPLATE COMPONENT AND METHOD OF USING SAME DURING HIP ARTHROPLASTY, which is hereby incorporated by reference in its entirety.

Once completed, the electronic surgical plan created at the Plan Development client 112 by the surgical planner may transmitted to the Planning server 102, and stored on the Planning server 102, as indicated at block 618. The electronic surgical plan may be stored in the respective ordering surgeon folder 324 in a secure manner, so that it is accessible only by the ordering surgeon and/or his staff. Specifically, the surgical planner may access and login to the Planning server 102 from the Plan Development client 112.

Figure 9:
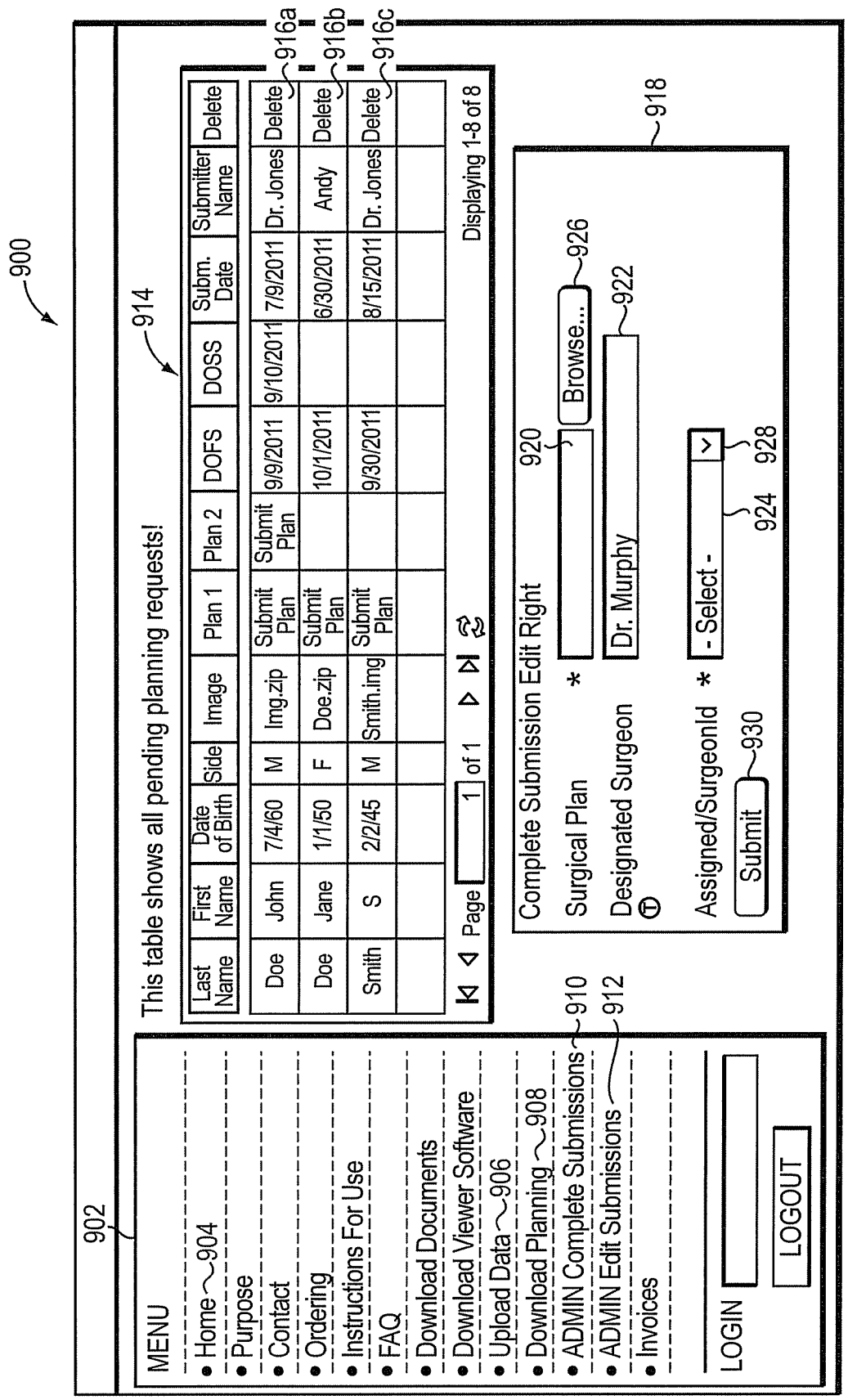
FIG. 9 is a schematic illustration of a surgical plan upload web page in accordance with an embodiment of the present invention.

FIG. 9 is schematic illustration of a surgical plan upload web page 900 for presentation on the Plan Development client 112. The surgical plan upload page 900 includes the navigation menu 902 having a plurality of navigation buttons, such as a Home button 904, an Upload Data button 906, a Download Planning button 908, an Administrator (ADMIN) Complete Submissions button 910, and an ADMIN Edit is Submissions button 912. The upload page 900 may be presented in response to the selection of an ADMIN complete submissions button 910 by the surgical planner after logging in. The web page 900 may include a first region 914 that lists one or more requests for surgical plans that are pending. For example, first region 914 may include a plurality of entries, such as entries 916*a-c*, where each entry corresponds to a pending request for a surgical plan. To associate a completed plan with a particular request, the planning surgeon may select the desired request, for example entry 916*a*, from the first region 914. Selection may be made with a mouse or other pointing device.

In response, the web-based facility 306 may present a dialog box 918 for receiving a designation of the surgical plan for the identified record. The dialog box 918 may include one or more fields for receiving information from the planning surgeon operating through the Plan Development client 112. Specifically, the dialog box 918 may include a Surgical Plan field 920, a Designated Surgeon field 922, and an Assigned Surgeon ID field 924. The surgical planner enters the path and file name for the surgical plan that was created in the Surgical Plan field 908. The Surgical Plan field 908 may include a "Browse" or other command button 926, which if selected by the surgical planner, presents a dialog box (not shown) that allows the surgical planner to navigate through the directories and folders located on the Plan Development client 112 (or on computers, servers or other data processing machines accessible from it) in order to select one or more surgical plans to be uploaded to the Planning server 102.

The Designated Surgeon field 922 may present the name of the surgeon as entered by the technician in the Assigned Surgeon field 724 of the request web page 700, and stored in field 820 of the planning record 320. In an embodiment, the planning surgeon may utilize the information presented in the Designated Surgeon field 922 to identify the surgeon performing the procedure on the patient by his or her user name (or other registered name) within the Assigned Surgeon ID field 924. A drop down button 928 may be provided that, when selected, provides a list (not shown) of all registered users to assist the surgical planner in selecting the correct name.

The surgical plan upload page 900 may also include a Submit or other command button 930 that may be selected by the surgical planner, after identifying the surgical plan file and entering the requested information. In response to entering the submit command 930, the upload/down engine 918 uploads the surgical plan created by the planning surgeon to the planning server 102. In addition, the content management system 310 may populate the planner user ID field 824 (FIG. 8), the path/file name of surgical plans fields 826, 828, and the surgeon ID field 830 of the respective planning record 320.

In an embodiment, the surgical plan may be stored in an operating surgeon folder 324 associated with the surgeon that will be performing the procedure.

The content management system 310 cooperates with the email service 312 to generate and send one or more notifications to the ordering surgeon, informing him or her that a surgical plan has been prepared and is now available for download from the Planning server 102, as indicated at block 620.

The ordering surgeon may utilize the Ordering Surgeon client 108 and/or the OR client 110 to access and download the surgical plan, which is stored in his or her operating surgeon folder 324, as indicated at block 622.

FIG. 10 is schematic illustration of a surgical plan download web page 1000 for presentation on the Ordering Surgeon client 108 and/or the Operating Room client 110. The surgical plan download page 1000 may be presented in response to the selection of a Download planning button, such as button 908 (FIG. 9) on a navigation menu, such as menu 902. The web page 1000 may include one or more search fields, such as a Patient Last name search field 1002, and a Planned side search field 1004. The web page may also include a Submit or other command button 1006, and a surgical plan listing region 1008. The surgeon may search for a particular plan by entering search criteria in the one or more search fields 1002, 1004, and selecting the submit button 1006. In response, the content management system 310 searches the plans in the respective operating surgeon folder 324, and presents the matching plan(s) in the surgical plan listing region 1008. In an embodiment, the surgeon may leave the one or more search fields 1002, 1004 blank and simply select the Submit button 1006. In response, the content management system 310 may provide a listing of all of the surgical plans from the respective operating surgeon folder 324 in the surgical plan listing region 1008.

Each surgical plan listed in the surgical plan listing region 1006 may be included in an entry, such as entries 1010*a*, 1010*b* that include information concerning the plan, such as the patient's first and last name, the area to be operated on, e.g., left or right side for a THR operation, etc. In addition, each entry may include a hyperlink that is linked to the respective surgical plan as sorted in the file system 314 of the Planning server 102. To download a desired surgical plan, the ordering surgeon may select the hyperlink, e.g., StevensRtPlan.zip from entry 1010*a*. In response, the upload/download engine 318 of the Planning server 102 may present a dialog box at the Order Surgeon client 108 that allows the requesting surgeon to select a particular directory path/file name for storing the surgical plan on the Ordering Surgeon client 108 and/or the Operating Room client 110.

The upload/download engine 318 may then download the selected surgical plan into the identified directory/folder path.

In an embodiment, the Ordering Surgeon client 108 may run a viewer software module that presents the electronic surgical plan, e.g., on a display of the Ordering Surgeon client 108. The ordering surgeon may operate the viewer software to review and/or adjust the surgical plan before or even during the surgical procedure. For example, a combined anteversion goal can be adjusted by the ordering surgeon once the anteversion of the femoral stem is determined in surgery. That is, the ordering surgeon may select and/or adjust one or more surgical instruments as provided in the surgical plan. In addition, to the extent the surgical plan includes one or more executable files, the surgeon or a technician may load the executable files in a respective machine or device for execution during the surgical procedure, or may use the files in a 3D printer to build a patient-specific component at the hospital or at a local manufacturing facility.

Alternatively, the Planning server 102 or another server may run the viewer software, and the ordering surgeon may access it through a web browser application. In this embodiment, the surgical plan is not downloaded to the Ordering Surgeon client 108 or the OR client 110. Instead, the surgical plan remains on the Planning server 102 and is accessed through the web-based facility 306, and a surgical plan view module, which may be similar to module 404, running on the Planning server 102.

The ordering surgeon may load the surgical plan on the Operating Room client 110, and access the electronic surgical plan during the surgical procedure. Alternatively, the ordering surgeon may use the Operating Room client 110 to access the electronic surgical plan from the Planner server 102. Further, the surgeon or a technician may establish a data communication link or channel to a robotic or other surgical device or a 3D printer, which may then be controlled remotely through instructions issued from the Planning server according to the surgical plan.

Figure 11:
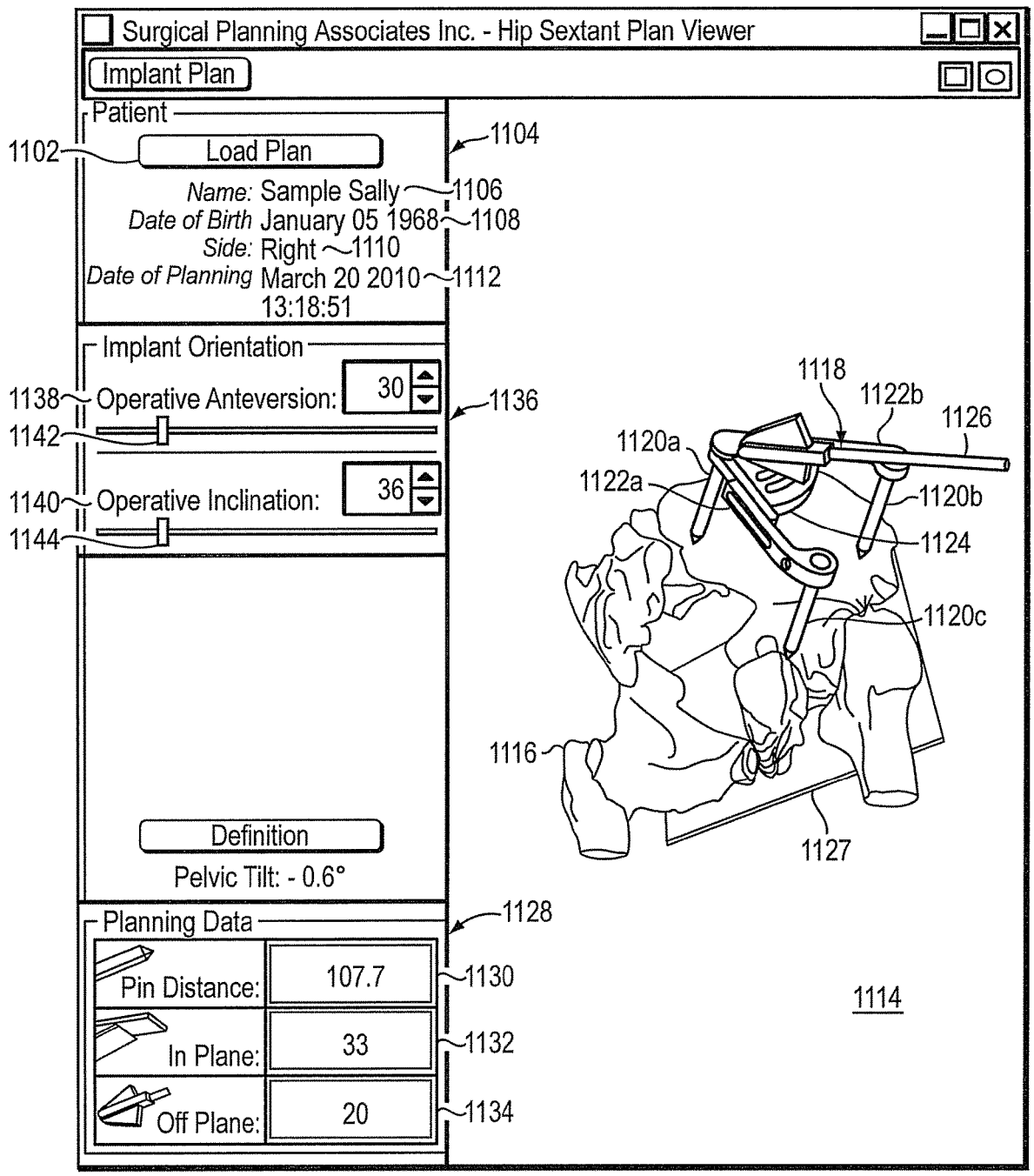
FIG. 11 is a schematic illustration of a surgical plan in accordance with an embodiment of the present invention.

FIG. 11 is a schematic illustration of a surgical plan 1100 as presented by the surgical plan view module 404 (FIG. 4). The surgical plan 1100 may have a Load Plan command button 1102 for selecting a plan to be opened by the module 404. In response to a user selecting the Load Plan button 1102, the module 404 may display a dialog box (not shown) allowing the user to navigate available directories and files and select a surgical plan file to be opened. The selected plan to be opened may be the surgical plan downloaded to the client on which the module 404 is running, such as the OR client 110, the Ordering Surgeon client 108, or the Sales Representative client 110, among others. The surgical plan 110 may also include a first region 1104 containing information regarding the particular plan, such as a Patient name entry 1106, a Patient date of birth entry 1108, a region to be operated on entry 1110, for example the patient's right side, and a Date of Planning entry 1112.

The surgical plan may include a viewing area 1114. The viewing area may include an image of the patient's anatomy to be operated on. For example, for THR surgery, the viewing area may include a three-dimensional image of the patient's pelvis 1116. In addition, an image of a surgical instrument to be used during the procedure, such as instrument image 1118, may be included in the viewing area 1114. The instrument represented by image 1118 may be a mechanical instrument having a plurality of parts or elements. For example, the instrument may have three legs 1120*a-c*, two arms 1122*a-b*, a guide pin support structure 1124, and a guide pin 1126. The viewing area 1114 may also include one or more reference elements, such as an Anterior/Posterior plane 1127 of the pelvis 1116.

The surgical plan 1100 also may include a planning data region 1128 that includes one or more data elements determined by the surgical planner, and included in the surgical plan. In an embodiment, the data elements specify one or more adjustments to be made to the surgical instrument 1118, for example, to fit the surgical instrument to the particular patient, and to achieve one or more objectives of the surgical procedure. For example, the planning data region may include a pin distance data value 1130. This value may specify the distance between legs 1120a and 1120c and between legs 1120a and 1120b. The ordering surgeon may adjust the physical instrument used during surgery to achieve this distance by adjusting the two arms 1122a, 1122b of the instrument 1118 to the specified pin distance value, e.g., "107.7". The planning data region 1128 may also include an In Plane data value 1132. This value may specify the angle, e.g., 33 degrees, from arm 1122a that the guide pin support structure 1124 is to be located. The planning data region 1128 may further include an Off Plane data value 1134. This value may specify the angle, e.g., 20 degrees, that the guide pin 1126 is raised above a plane defined by the two arms 1122a, 1122b.

The surgical plan 1100 may also include a surgical objectives region 1136, which may specify one or more objectives to be achieved by the surgical plan. For example, in THR surgery, one of the surgical objectives may be the orientation of an acetabular cup inserted into the patient's acetabular. The orientation, moreover, may be specified in terms of anteversion and inclination. Accordingly, the surgical objections region 1136 may include an operative anteversion entry 1138, and an operative inclination entry 1140. By adjusting the surgical instrument 1118 according to the values specified in the planning data region 1128, the guide pin 1126 on the instrument 1118 may be used by the ordering surgeon during the procedure in order to insert the acetabular cup in accordance with the surgical objectives specified in the surgical objectives region 1136, namely an anteversion of 30 and an inclination of 36. During the creation of the surgical plan, the surgical planner may determine the one or more surgical objectives, and the one or more data plan elements for achieving the objectives.

In an embodiment, the surgical plan may be a preliminary plan. That is, one or more of the surgical objectives may be modified by the ordering surgeon. That is, the ordering surgeon may change one or more of the surgical objectives. For example, the ordering surgeon may modify the anteversion and/or the inclination. The surgical objectives region 1136 may include one or more sliders, data entry boxes, arrows, or other graphical elements, such as slider elements 1142 and 1144 that may be used to modify the respective surgical objectives. In an embodiment, if the ordering surgeon changes one or more of the surgical objectives, such as the anteversion, the surgical plan view module 404 may be configured to recalculate one or more of the data elements in the planning data region 1128 in order to achieve the new objective. For example, if the ordering surgeon changes the desired anteversion or inclination, then the viewer module 404 may compute new in plane and off plan values to achieve those new desired surgical objectives.

It should be understood that one or more objectives or elements of the surgical plan may be locked, such as the pin distance, while other objectives or data plan elements may be modifiable by the ordering surgeon.

In another embodiment, the surgical objectives and/or the planning data values may be fixed.

In an embodiment, an entity, such as a corporation, may run the surgical planning services of the present invention. That is, the surgical planning company may own and/or rent the Planning server and the Plan Development client. The surgical planning company may also own and/or license software running on the Planning server and Plan Development client. The surgical planning company may charge ordering surgeons, hospitals, patients, medical insurers or others for the service of creating an electronic, patient-specific surgical plan, and use of associated instruments that may reside or be shipped to or printed at the facility to carry out the surgical plan, such as a mechanical or other surgical instrument or a component.

Using the surgical plan, the ordering surgeon may perform the surgical procedure on the patient, as indicated at block 624 (FIG. 6B).

Following the surgical procedure, a notification may be sent to the Planning server 102, indicating that the procedure was performed and the date it was performed, as indicated at block 626. The notification may be sent by a sales representative from the Sales Rep client 116, or by the ordering surgeon. The notification may identify the patient by name and date of birth. Alternatively or additionally, the notification may identify the surgical procedure by the unique plan number assigned to the surgical plan. The Planning server 102 receives the notification, as indicated at block 628. In response to the notification, the content management system 310 may automatically generate an invoice for services relating to the creation of the surgical plan, as indicated at block 630. The content management system 310 may cooperate with the email service 312 to send the invoice automatically to the ordering surgeon or his or her hospital or medical center, as also indicated at block 630.

In an embodiment, the content management system 310 may cause a dialog box to appear at the time the surgical plan is downloaded by the ordering surgeon, for example, to the Ordering Surgeon client 108 or the Operating Room client 110. The dialog box may include a data entry field requesting the name of the facility at which the surgical procedure will be performed, e.g., the name of the hospital or medical facility. The surgeon may enter the name, and submit this information to the Planning server 102.

The content management system 310 may consider the downloading of the surgical plan by the ordering surgeon as a "billable event". In this case, upon receiving the name of the hospital or medical facility at which the surgical procedure will be performed, the content management system 310 may generate automatically an invoice to the identified hospital or medical facility. The content management system 310 may include within the generated invoice a price that reflects a negotiated or agreed-on price with the particular hospital or medical facility. Specifically, the content management system 310 may store negotiated or agreed-on prices with a plurality of different hospitals and medical facilities. This information may be stored, for example, in the file system 314. The content management system 310 in cooperation with the email service 312 may generate an email including the invoice and issue it to the hospital or medical facility identified by the ordering surgeon. Payments received at the Planning server 102 may be reconciled, and paid invoices closed. The content management system 310 may automatically generate and issue a notification concerning unpaid invoices, for example, invoices un-paid after 30 days, 60 days or some other period.

A copy of the invoice may also be stored in the file system 314. The invoice may be assigned an invoice number by the content management system 310. Using the invoice number or other identifying information, the content management system 310 may reconcile electronic payments received at the Planning server 102, such as direct bank payments, to the invoices. An administrator may periodically query the Planning server 102 to identify any outstanding invoices.

In an embodiment, the charge for creating one or more patient-specific surgical plans can be incorporated into a charge for the one or more surgical instruments utilized during the surgical procedure.

The foregoing description of embodiments is intended to provide illustration and description, but is not intended to be exhaustive or to limit the invention to the precise form disclosed. Modifications and variations are possible in light of the above teachings or may be acquired from a practice of the invention. For example, while a series of acts has been described above with respect to the flow diagrams, the order of the acts may be modified in other implementations. Further, non-dependent acts may be performed in parallel. Also, the term "user", as used herein, is intended to be broadly interpreted to include, for example, a computer or data processing system or a user of a computer or data processing system, unless otherwise stated.

Further, certain embodiments of the invention may be implemented as logic that performs one or more functions. This logic may be hardware-based, software-based, or a combination of hardware-based and software-based. Some or all of the logic may be stored in one or more tangible non-transitory computer-readable storage media and may include computer-executable instructions that may be executed by a computer or data processing system, such as server system 102. The computer-executable instructions may include instructions that implement one or more embodiments of the invention. The tangible non-transitory computer-readable storage media may be volatile or non-volatile and may include, for example, flash memories, dynamic memories, removable disks, and non-removable disks.

No element, act, or instruction used herein should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

The foregoing description has been directed to specific embodiments of the present invention. It will be apparent, however, that other variations and modifications may be made to the described embodiments, with the attainment of some or all of their advantages. For example, the surgical plan may be a template that is completed by the ordering surgeon. Therefore, it is the object of the appended claims to cover all such variations and modifications as come within the true spirit and scope of the invention.

What is claimed is:

1. A method comprising:
   creating, by a device, a computer-implemented two-dimensional (2D) or a three-dimensional (3D) surface model of a portion of a patient's anatomy from information contained in one or more electronic data files, wherein the one or more electronic data files is at least one of a computed tomography (CT) image, a magnetic resonance image (MRI), or an X-ray image of the patient;
   analyzing the computer-implemented 2D or 3D surface model to determine at least one of a dimension, a size, or a shape of the portion of the patient's anatomy;
   calculating one or more adjustments to be made to an adjustable, mechanical surgical instrument to fit the adjustable, mechanical surgical instrument to the portion of the patient's anatomy, wherein the calculating is based on the at least one of the dimension, the size, or the shape;
   generating an electronic surgical plan for the patient, the electronic surgical plan including instructions for performing a surgical procedure on the patient, where the instructions
      are customized to the patient based on the one or more electronic data files, and
      specify the one or more adjustments to be made to the adjustable, mechanical surgical instrument; and
   displaying, on a computer display, at least a portion of the electronic surgical plan including the one or more adjustments to be made to the adjustable, mechanical surgical instrument,
      wherein the adjustable, mechanical surgical instrument is suitable for reuse with different patients based on different adjustments that are made to the adjustable, mechanical surgical instrument.

2. The method of claim 1 further comprising:
   notifying an ordering surgeon of the availability of the electronic surgical plan.

3. The method of claim 2 wherein the ordering surgeon is notified by at least one of an email message, a text message, or a voice message.

4. The method of claim 1 wherein the one or more electronic data files are produced as part of a diagnostic procedure performed on the patient before the surgical procedure.

5. The method of claim 1 wherein the one or more adjustments specified in the electronic surgical plan are modifiable by an ordering surgeon.

6. The method of claim 1 wherein
   the electronic surgical plan further includes one or more instructions for constructing a patient-specific component for use during the surgical procedure.

7. The method of claim 6 wherein the patient-specific component is a drill guide.

8. The method of claim 1 wherein
   the one or more electronic data files include information regarding a hip of the patient, and
   the one or more adjustments specified in the electronic surgical plan cause the adjustable, mechanical surgical instrument to fit to the hip of the patient.

9. The method of claim 8 further comprising fitting the adjustable, mechanical surgical instrument to the hip of the patient to perform the surgical procedure.

10. The method of claim 9 wherein the one or more adjustments specified in the surgical plan specify a setting for a guide pin for orienting a prosthetic acetabular cup component inserted into the hip of the patient.

11. The method of claim 1 further comprising modifying the electronic surgical plan by an ordering surgeon.

12. The method of claim 1 wherein the instructions include machine instructions and wherein the adjustable, mechanical surgical instrument is robotic, the method further comprising:
   adjusting the adjustable, mechanical surgical instrument based on the adjustments and utilizing the machine instructions; and utilizing the machine instructions by the adjustable, mechanical surgical instrument to perform the surgical procedure.

13. A system for generating an electronic surgical plan, the system comprising:
one or more processors configured to:
create a computer-implemented two-dimensional (2D) or a three-dimensional (3D) surface model of a portion of a patient's anatomy from information contained in one or more electronic data files, wherein the one or more electronic data files is at least one of a computed tomography (CT) image, a magnetic resonance image (MRI), or an X-ray image of the patient;
analyze the computer-implemented 2D or 3D surface model to determine at least one of a dimension, a size, or a shape of the portion of the patient's anatomy;
calculate one or more adjustments to be made to an adjustable, mechanical surgical instrument to fit the adjustable, mechanical surgical instrument to the portion of the patient's anatomy, wherein the calculating is based on the at least one of the dimension, the size, or the shape;
generate an electronic surgical plan for the patient, the electronic surgical plan including instructions for performing a surgical procedure on the patient, where the instructions
are customized to the patient based on the one or more electronic data files, and
specify the one or more adjustments to be made to the adjustable, mechanical surgical instrument; and
display, on a computer display, at least a portion of the electronic surgical plan including t the one or more adjustments to be made to the adjustable, mechanical surgical instrument,
wherein the adjustable, mechanical surgical instrument is suitable for reuse with different patients based on different adjustments that are made to the adjustable, mechanical surgical instrument.

14. The system of claim 13 wherein the one or more processors are further configured to:
fit the adjustable, mechanical surgical instrument to a hip of the patient to perform the surgical procedure.

15. The system of claim 14 wherein the one or more adjustments specified in the surgical plan specify a setting for a guide pin for orienting a prosthetic acetabular cup component inserted into the hip of the patient.

16. The system of claim 13 wherein the instructions include machine instructions and the adjustable, mechanical surgical instrument is robotic, and wherein the one or more processors are further configured to:
adjust the adjustable, mechanical surgical instrument based on the adjustments and utilizing the machine instructions, and
utilize the machine instructions by the adjustable, mechanical surgical instrument to perform the surgical procedure.

17. A non-transitory computer-readable medium comprising program instructions, the program instructions when executed by a processing element operable to:
create a computer-implemented two-dimensional (2D) or a three-dimensional (3D) surface model of a portion of a patient's anatomy from information contained in the one or more electronic data files, wherein the one or more electronic data files is at least one of a computed tomography (CT) image, a magnetic resonance image (MRI), or an X-ray image of the patient;
analyze the computer-implemented 2D or 3D surface model to determine at least one of a dimension, a size, or a shape of the portion of the patient's anatomy;
calculate one or more adjustments to be made to an adjustable, mechanical surgical instrument to fit the adjustable, mechanical surgical instrument to the portion of the patient's anatomy, wherein the calculating is based on the at least one of the dimension, the size, or the shape;
generate an electronic surgical plan for the patient, the electronic surgical plan including instructions for performing a surgical procedure on the patient, where the instructions
are customized to the patient based on the one or more electronic data files, and
specify the one or more adjustments to be made to the adjustable, mechanical surgical instrument; and
display, on a computer display, at least a portion of the electronic surgical plan including the one or more adjustments to be made to the adjustable, mechanical surgical instrument,
wherein the adjustable, mechanical surgical instrument is suitable for reuse with different patients based on different adjustments that are made to the adjustable, mechanical surgical instrument.

18. The non-transitory computer-readable medium of claim 17 wherein the program instructions when executed by the processing element further operable to:
fit the adjustable, mechanical surgical instrument to a hip of the patient to perform the surgical procedure.

19. The non-transitory computer-readable medium of claim 18 wherein the one or more adjustments specified in the surgical plan specify a setting for a guide pin for orienting a prosthetic acetabular cup component inserted into the hip of the patient.

20. The non-transitory computer-readable medium of claim 17 wherein the instructions include machine instructions and the adjustable, mechanical surgical instrument is robotic, and wherein the program instructions when executed by the processing element further operable to:
adjust the adjustable, mechanical surgical instrument based on the adjustments and utilizing the machine instructions; and
utilize the machine instructions by the adjustable, mechanical surgical instrument to perform the surgical procedure.

* * * * *